US005599709A

United States Patent [19]
Lindstrom et al.

[11] Patent Number: 5,599,709
[45] Date of Patent: Feb. 4, 1997

[54] RECOMBINANT DNA ENCODING NEURONAL α-BUNGAROTOXIN-BINDING PROTEINS

[75] Inventors: Jon M. Lindstrom, Del Mar; Ralf D. Schoepfer, La Jolla, both of Calif.

[73] Assignee: The Salk Institute for Biological Studies, San Diego, Calif.

[21] Appl. No.: 413,947

[22] Filed: Sep. 28, 1989

[51] Int. Cl.⁶ .............. C12N 1/21; C12N 5/10; C12N 15/12

[52] U.S. Cl. .............. 435/252.3; 435/320.1; 435/69.1; 536/23.5

[58] Field of Search .............. 435/69.1, 252.3, 435/320.1; 436/501; 536/27

[56] References Cited

PUBLICATIONS

Kao, et al., "Identification of the α Subunit Half–cystine Specifically Labelled by an Affinity Reagent for the Acetylcholine Receptor Binding Site", J. Biol. Chem. 259, 11662–11665 (1984).

Kao, et al., "Acetylcholine Receptor Binding Site Contains a Disulfide Cross–link Between Adjacent Half–Cystinyl Residues", J. Biol. Chem. 261, 8085–8088 (1986).

Whiting, et al., "Affinity Labelling of Neuronal Acetylcholine Receptors Localizes Acetylcholine–binding Sites to Their β–subunits", FEBS Lett. 213, 55–60 (1987).

Whiting, et al., "Neuronal Nicotinic Acetylcholine Receptor β–subunit is Coded for by the cDNA Clone α₄" FEBS Lett. 219, 459–463 (1987).

Jacob, et al., "Surface and Intracellular Distribution of a Putative Neuronal Nicotinic Acetylcholine Receptor", J. Cell. Biol. 103, 205–214 (1986).

Lindstrom, et al., "Molecular Studies of the Neuronal Nicotinic Acetylcholine Receptor Family", Mol. Neurobiol., 1, pp. 281–337 (1987).

Carbonetto, et al., "Nonequivalence of α–bungarotoxin Receptors and Acetylcholine Receptors in Chick Sympathetic Neurons", Proc. Natl. Acad. Sci. USA, 75, pp. 1016–1020 (1978).

Schoepfer, et al., "Structure of Muscle and Neuronal Nicotinic Acetylcholine Receptors", NATO–ASI Series H(32), pp. 37–53 (1989).

Whiting, et al., "Characterization of Bovine and Human Neuronal Nicotinic Acetylcholine Receptors Using Monoclonal Antibodies", J. Neurosci. 8, pp. 3395–3404 (1988).

Wada, et al., "Distribution of Alpha2, Alpha3, Alpha4, Beta2 Neuronal Nicotinic Receptor Subunit mRNAs in the Central Nervous System: A Hybridization Histochemical Study in the Rat", J. Comp. Neurol. 284, pp. 314–335 (1989).

Barnard, et al., "Molecular Biology of the GABA$_A$ Receptor: The Receptor/Channel Superfamily", Trends Neurosci. 10, 502 (1987).

Peralta, et al., "Structural Basis of Muscarinic Acetylcholine Receptor Subtype Diversity", TIPS–Feb. 1988 Supplement, pp. 6–11.

(List continued on next page.)

Primary Examiner—John Ulm
Attorney, Agent, or Firm—Fitch, Even, Tabin & Flannery

[57] ABSTRACT

An isolated DNA molecule encoding an α-bungarotoxin-binding protein (αBgtBP) subtype or a fragment of such α subunit is provided. The fragment of the α subunit is sufficiently homologous to specified DNA (FIG. 2A or FIG. 2B) so as to hybridize thereto under conditions of low stringency. Identification, characterization, isolation and sequencing of cDNA clones which encode two neuronal αBgtBP subunits, α1 and α2, is made possible. Such clones may be used as probes to identify further neuronal αBgtBP subunits, or as diagnostic tools to screen cholinergic agents and other drugs that may affect ligand binding, ion channel or other activity of intact neuronal αBgtBP subtypes.

22 Claims, 9 Drawing Sheets

OTHER PUBLICATIONS

Frielle, et al., "Structural Basis of β-adrenergic Receptor Subtype Specificity Studied with Chimeric $\beta_1/\beta_2$-adrenergic Receptors", Proc. Natl. Acad. Sci. USA, 85, 9494–9498 (1988).

Clarke, et al., "Nicotinic Binding in Rat Brain: Autoradiographic Comparison of [$^3$H]Acetylcholine, [$^3$H]Nicotine, and [$^{125}$I]-α-Bungarotoxin", J. Neurosci. 5, 1307–1315 (1985).

Patrick, et al., "α-Bungarotoxin Binding and Cholinergic Receptor Function on a Rat Sympathetic Nerve Line", J. Biol. Chem. 252, 8629–8633 (1977).

Smith, et al., "Differential Regulation of Acetylcholine Sensitivity and α-Bungarotoxin-Binding Sites on Ciliary Ganglion Neurons in Cell Culture", J. Neurosci. 3, 2395–2402 (1983).

Jacob, et al., "The Ultrastructural Localization of α-Bungarotoxin Binding Sites in Relation to Synapses on Chick Ciliary Ganglion Neurons", J. Neurosci. 3, 260–271 (1983).

Conti–Tronconi, et al., "Brain and Muscle Nicotinic Acetylcholine Receptors are Different but Homologous Proteins", Proc. Natl. Acad. Sci. USA, 82, 5208–5212 (1985).

Whiting, et al., "Purification and Characterization of a Nicotinic Acetylcholine Receptor from Rat Brain", Proc. Natl. Acad. Sci. USA 84, 595–599 (1987).

Norman, et al., "Nicotinic Acetylcholine Receptor from Chick Optic Lobe", Proc. Natl. Acad. Sci. USA, 79, 1321–1325 (1982).

P.N.A.S. 78:6613–6617, Nov. 1981, Suggs et al. Use of synthetic oligonucleotides as hybridization probes: Isolation of cloned cDNA sequences for human $\beta_2$–microglobulin.

FEBS Letts. 226:235–240, Jan. 1988, Schoepfer et. al. The human medulloblastoma cell line TE 671 expresses a muscle–like acetylcholine receptor.

P.N.A.S. 84:5967–5971, Aug. 1987, Claudio Stable expression of transfected *Torpedo* acetylcholine receptor α subunits in mouse fibroblasts.

cDNA αBgtBP α1    GEFQRKLYKELLKNYNPLERPVAND...
protein           XEFETKLYKELLKNYNPLEXPVAXD
cDNA αBgtBP α2    GESQRRLYRDLLRNYNRLERPVMND...

```
...CCATTACTGCATTGCTGACCACTCACAGTGTTCATCTCCATGCTTGACAGGCTGCTGCCGG
              -120                -100               -80
       -20                    -10                              -1
       MetGlyLeuArgAlaLeuMetLeuTrpLeuLeuAlaAlaAlaGlyLeuValArgGluSerLeuGln
GCTCCCGGAATGGGCCTCCGGGCGCTGATGCTGTGGCTGCTGGCGGCGGCGGGGCTCGTGCGCGAGTCCCTGCAA
    -60              -40                -20                -1
                         10                       20
GlyGluPheGlnArgLysLeuTyrLysGluLeuLeuLysAsnTyrAsnProLeuGluArgProValAlaAsnAsp
GGAGAGTTCCAAAGGAAGCTGTACAAGGAGCTGCTGAAGAACTACAACCCTCTGGAACGACCAGTTGCAAATGAC
1                20                 40                 60
              30                                40                       50
SerGlnProLeuThrValTyrPheThrLeuSerLeuMetGlnIleMetAspValAspGluLysAsnGlnValLeu
TCCCAGCCGCTCACTGTCTATTTCACTCTCAGCCTCATGCAGATCATGGATGTGGATGAAAAGAATCAAGTATTA
        80                100                120                 140
                          60                              70
ThrThrAsnIleTrpLeuGlnMetTyrTrpThrAspHisTyrLeuGlnTrpAsnValSerGluTyrProGlyVal
ACAACAAACATCTGGCTACAAATGTACTGGACAGATCATTACTTACAGTGGAATGTGTCTGAATACCCTGGAGTG
            160                180                200                 220
                    80                          90                      100
LysAsnValArgPheProAspGlyLeuIleTrpLysProAspIleLeuLeuTyrAsnSerAlaAspGluArgPhe
AAGAACGTCCGTTTTCCTGATGGACTGATTTGGAAGCCAGATATTCTTCTCTATAACAGTGCTGATGAAAGATTT
            240                260                280                 300
                        110                       120
AspAlaThrPheHisThrAsnValLeuValAsnSerSerGlyHisCysGlnTyrLeuProProGlyIlePheLys
GATGCTACATTTCACACTAATGTTTTAGTCAATTCTTCGGGACACTGCCAATATCTGCCACCAGGCATATTTAAA
            320                340                 360
                    130                     140                       150
SerSerCysTyrIleAspValArgTrpPheProPheAspValGlnLysCysAsnLeuLysPheGlySerTrpThr
AGCTCATGCTACATAGACGTGCGTTGGTTTCCATTTGATGTTCAGAAGTGCAATCTGAAGTTTGGATCTTGGACA
        380                400                420                 440
                            160                           170
TyrGlyGlyTrpSerLeuAspLeuGlnMetGlnGluAlaAspIleSerGlyTyrIleSerAsnGlyGluTrpAsp
TATGGAGGCTGGTCCTTAGACTTACAAATGCAAGAAGCAGATATATCCGGCTATATTTCAAATGGAGAGTGGGAT
            460                480                500                 520
                    180                     190                       200
LeuValGlyIleProGlyLysArgThrGluSerPheTyrGluCysCysLysGluProTyrProAspIleThrPhe
TTAGTAGGAATTCCTGGAAGAGAACTGAGAGCTTTTATGAGTGCTGTAAAGAACCATACCCAGATATCACATTC
            540                560                580                 600
                        210                       220
ThrValThrMetArgArgArgThrLeuTyrTyrGlyLeuAsnLeuLeuIleProCysValLeuIleSerAlaLeu
ACAGTAACCATGAGACGCAGAACTCTCTACTACGGGCTCAACCTTCTTATTCCCTGTGTACTGATATCAGCACTT
            620                640                 660
              230                        240                         250
AlaLeuLeuValPheLeuLeuProAlaAspSerGlyGluLysIleSerLeuGlyIleThrValLeuLeuSerLeu
GCCTTATTAGTCTTTCTGCTTCCAGCAGACTCAGGAGAAAAGATCTCACTAGGTATAACAGTTTTATTGTCTCTC
        680                700                720                 740
                        260                         270
ThrValPheMetLeuLeuValAlaGluIleMetProAlaThrSerAspSerValProLeuIleAlaGlnTyrPhe
ACCGTCTTCATGTTACTCGTGGCTGAAATTATGCCAGCAACATCTGATTCTGTGCCCTTAATTGCTCAGTATTTT
            760                780                800                 820
                    280                       290                     300
AlaSerThrMetIleIleValGlyLeuSerValValValThrValIleValLeuGlnTyrHisHisHisSerAspPro
GCCAGCACCATGATTATTGTTGGCCTCTCTGTTGTTGTCACTGTTATCGTTCTACAATACCATCATCACGATCCA
        840                860                 880                 900
                        310                        320
AspGlyGlyLysMetProLysTrpThrArgValIleLeuLeuAsnTrpCysAlaTrpPheLeuArgMetLysArg
GATGGGGGAAAAATGCCTAAATGGACAAGAGTCATCCTTCTGAATTGGTGTGCTTGGTTTCTGAGGATGAAGAGA
            920                 940                 960
                        330                       340                       350
ProGlyGluAspLysValArgProAlaCysGlnHisLysGlnArgArgCysSerLeuSerSerMetGluMetAsn
CCAGGGGAAGATAAAGTGCGTCCCGCCTGTCAACATAAACAGCGCCGATGCAGCCTGTCAAGCATGGAGATGAAC
        980                1000                1020                1040
                        360                               370
ThrValSerGlyGlnGlnCysSerAsnGlyAsnMetLeuTyrIleGlyPheArgGlyLeuAspGlyValHisCys
ACTGTGAGTGGTCAGCAATGCAGTAATGGGAACATGCTGTATATTGGGTTTCGAGGGCTGGATGGGGTTCACTGC
            1060                1080                1100                 1120
```

FIG.2A

```
                380                                    390                                    400
ThrProThrThrAspSerGlyValIleCysGlyArgMetThrCysSerProThrGluGluGluAsnLeuLeuHis
ACACCCACCACTGATTCAGGGGTGATCTGTGGGAGGATGACCTGTTCACCAACAGAGGAAGAAAATCTTCTGCAC
                1140                   1160                   1180                   1200
                                    410                                    420
SerGlyHisProSerGluGlyAspProAspLeuAlaLysIleLeuGluGluValArgTyrIleAlaAsnArgPhe
AGTGGCCACCCCTCTGAAGGCGACCCAGATTTGGCTAAGATCCTGGAAGAGGTCAGATACATTGCAAACAGGTTC
                1220                   1240                   1260
                430                                    440                                    450
ArgAspGlnAspGluGluGluAlaIleCysAsnGluTrpLysPheAlaAlaSerValValAspArgLeuCysLeu
AGAGACCAGGATGAAGAAGAAGCCATTTGCAACGAATGGAAGTTTGCAGCCTCTGTAGTAGATCGGCTCTGCTTG
                1280                   1300                   1320                   1340
                                    460                                    470
MetAlaPheSerValPheThrIleIleCysThrIleGlyIleLeuMetSerAlaProAsnPheValGluAlaVal
ATGGCATTTTCGGTCTTCACCATCATTTGTACAATTGGCATCTTAATGTCAGCACCAAACTTTGTAGAGGCTGTC
                1360                   1380                   1400                   1420
                480
SerLysAspPheAlaEnd
TCTAAAGATTTTGCTTAACTCCTAACTATGATTTGATTCTCTGAAGTATCATATGTAGCAAATAAGAGTGTATTT
                1440                   1460                   1480                   1500

TTTTTTGTTTGTTTGCTTGTTTTTAATGAGTACACTGTATCTCATTGTCCTCTGTCTTTTGCCCTCCCCCCTATT
                1520                   1540                   1560

CCCCCAGCATTCCTCTGACCCTGGGCTCCTTTCTGAACAGGAGCACCCTTTCAGAAGGGGAGCCAGGGATCCCTC
     1580                   1600                   1620                   1640

CCTGGGCTGTATGCCCAGCTCCTCTAAGCACTTCGCTTTGGGAGATGCAAAGTGAGTGCAAGACCCTTCAGAATG
          1660                   1680                   1700                   1720

AAAGGATACTGCTCCAGCATCTTTTATGCATTTCAAACTGGCTAGTACATAAATTAATAGGTAGGTAATGCCAGA
              1740                   1760                   1780                   1800

AATGTCATTTCTTCCAGAATTTACTTTAAAAGATAGAAGTTAGCCCTATGTTTCGGACAGGATTAAATCTGAATG
               1820                   1840                   1860

AAAGGAAACTCAAACAGAAGAGGAAAAAAAGGGTAAGAACACCTTGCTTTTCAGTCTCTGGATGTTAGCGAGTAC
    1880                   1900                   1920                   1940

TGGGCTCACAGCTCACTCACAACCAGTCACATTTTAAATCCCTCAACGCATTTTACAGAGAGCTTATGTGAGTAT
         1960                   1980                   2000                   2020

ACAGGATTCTGATTTTGCCTGAGACTCCAGAAAGATGAAAGTCAAGATGAAACAGCACATATCTTGTCCTTCTGT
      2040                   2060                   2080                   2100

CACTTCCTGGACCTGACCTAGAAGTATGGCCTGGATTCTTAAAAAGGCATCACAGTAATTGCGGTGTTTATTACA
              2120                   2140                   2160

ACTCCCTTCTCTCCAGAAAAACATTCTTTCAACTAATGACTTCTGTCGGTTTTTACCCTTTACTGTGACATTAAA
    2180                   2200                   2220                   2240

AAAGTATTTACGATGGCTTTACCCTCATTTGTTAAAAAATATAATAATAAATTACACACAGTTGTCTCTCTACTT
          2260                   2280                   2300                   2320

TTCTACATTGAAATCCAGTTAACAGTAACTGTCTTGTACAGGCTCAAACATAATGACAGATCTAAAGCAAAAAAA
     2340                   2360                   2380                   2400

AAAAAACACATTAAATCATCAGATCCAGCTTTTCATTTCAATGTGAAATGTCTGATCTACTGTTTGCTTAGCCTT
               2420                   2440                   2460

TTATAGACTTCTTTTCATTGAGTCATCGTAACATATCCTAACAAGAAAACTGCATCCTTTCTGCTCAGTTTATCG
     2480                   2500                   2520                   2540

TACAAAGAACACTAATGAATTATAAATACTATATATAAACTATACATACATCCCAGGAAAGATTAAATCTTAAAT
          2560                   2580                   2600                   2620

AGGAATTC
```

FIG.2B

```
                                                                          -30
                                                                    MetLeuThrGluLys
          GAATTCATCTTCTTTTACCCTCTGCTCAGGAAAGGATAGACAGCCAGTTTGGACAATGCTTACTGAAAAG
             -140        -120         -100         -80
                   -20              -10                                     -1
        CysLeuGlyPhePheTyrSerGlyLeuCysLeuTrpAlaSerLeuPheLeuSerPhePheLysValSerGlnGln
        TGCTTGGGATTTTTTTATTCTGGACTGTGTCTGTGGGCATCCTTGTTCCTGTCTTTCTTTAAAGTATCTCAGCAG
              -60          -40         -20          -1
         1                    10                     20
        GlyGluSerGlnArgArgLeuTyrArgAspLeuLeuArgAsnTyrAsnArgLeuGluArgProValMetAsnAsp
        GGTGAAAGCCAGAGACGCTTGTACAGAGATCTGCTGAGAAACTACAATCGTCTGGAGCGCCCAGTCATGAATGAC
         1           20                   40                   60
                 30                    40                     50
        SerGlnProIleValValGluLeuGlnLeuSerLeuLeuGlnIleIleAspValAspGluLysAsnGlnValLeu
        TCCCAGCCCATTGTAGTTGAGCTTCAGCTTTCTTTGCTGCAGATAATTGATGTGGATGAGAAGAATCAGGTGTTG
             80                  100                  120                  140
                           60                     70
        IleThrAsnAlaTrpLeuGlnMetTyrTrpValAspIleTyrLeuSerTrpAspGlnTyrGluTyrProGlyVal
        ATTACAAATGCTTGGCTGCAGATGTACTGGGTTGATATTTACTTGTCTTGGGATCAGTACGAATACCCGGGTGTG
              160                 180                  200                 220
                     80                    90                    100
        GlnAsnLeuArgPheProSerAspGlnIleTrpValProAspIleLeuLeuTyrAsnSerAlaAspGluArgPhe
        CAGAACTTGCGATTTCCATCCGACCAGATTTGGGTACCTGATATTCTTCTCTATAACAGTGCGGATGAAAGATTC
              240                 260                  280                 300
                      110                    120
        AspAlaThrPheHisThrAsnValLeuValAsnTyrSerGlySerCysGlnTyrIleProProGlyIleLeuLys
        GATGCAACATTTCACACAAATGTGCTGGTGAATTACTCTGGATCCTGTCAATATATTCCTCCAGGCATTTTGAAG
              320                 340                 360
                      130                     140                     150
        SerThrCysTyrIleAspValArgTrpPheProPheAspValGlnLysCysAspLeuLysPheGlySerTrpThr
        AGCACATGTTACATTGATGTCCGCTGGTTCCCTTTTGATGTGCAGAAGTGTGATTTGAAGTTTGGCTCTTGGACT
              380                 400                 420                  440
                              160                     170
        HisSerGlyTrpLeuIleAspLeuGlnMetLeuGluAlaAspIleSerAsnTyrIleSerAsnGlyGluTrpAsp
        CACAGTGGTTGGCTGATTGACCTGCAGATGCTTGAGGCTGATATTTCCAACTACATCTCAAATGGAGAGTGGGAT
              460                 480                 500                  520
                  180                    190                    200
        LeuValGlyValProGlyLysArgAsnGluLeuTyrTyrGluCysCysLysGluProTyrProAspValThrTyr
        TTAGTGGGTGTCCCAGGAAAGAGGAATGAGTTGTACTATGAATGCTGTAAAGAACCATATCCAGATGTGACATAC
              540                 560                 580                  600
                         210                     220
        ThrIleThrMetArgArgArgThrLeuTyrTyrGlyLeuAsnLeuLeuIleProCysValLeuIleSerGlyLeu
        ACCATCACCATGCGACGACGCACTCTCTACTATGGCTTGAACCTACTGATTCCCTGTGTTCTCATATCTGGCTTG
              620                 640                  660
                     230                     240                     250
        AlaLeuLeuValPheLeuLeuProAlaAspSerGlyGluLysIleSerLeuGlyIleThrValLeuLeuSerLeu
        GCACTGCTTGTATTCCTTTTGCCTGCTGATTCAGGAGAGAAGATTTCTTTAGGTATCACTGTTCTGCTTTCCCTG
              680                 700                 720                  740
                           260                    270
        ThrValPheMetLeuLeuValAlaGluIleMetProAlaThrSerAspSerValProLeuIleAlaGlnTyrPhe
        ACTGTATTCATGCTGCTTGTGGCTGAGATCATGCCTGCAACTTCTGATTCAGTCCCACTAATAGCTCAGTATTTT
              760                 780                 800                  820
                       280                     290                    300
        AlaSerIleMetValIleValGlyLeuSerValValValThrValLeuValLeuGlnPheHisHisHisAspPro
        GCTAGCATCATGGTCATTGTTGGTCTGTCTGTGGTCGTAACGGTGCTGGTTCTGCAGTTTCACCACCATGACCCA
              840                 860                 880                  900
                          310                    320
        GlnAlaGlyLysMetProArgTrpValArgValIleLeuLeuAsnTrpCysAlaTrpPheLeuArgMetLysLys
        CAAGCAGGAAAGATGCCCAGATGGGTCCGTGTCATTCTGCTGAATTGGTGTGCTTGGTTTTTACGTATGAAAAAA
              920                 940                  960
                       330                     340                    350
        ProGlyGluAsnIleLysProLeuSerCysLysTyrSerTyrProLysHisHisProSerLeuLysAsnThrGlu
        CCTGGGGAAAATATAAAGCCCCTCTCTTGCAAATATAGCTATCCCAAACACCATCCAAGCCTGAAAAACACAGAG
              980                1000                 1020                 1040
                           360                     370
        MetAsnValLeuProGlyHisGlnProSerAsnGlyAsnMetIleTyrSerTyrHisThrMetGluAsnProCys
        ATGAATGTCCTACCTGGGCACCAGCCCAGCAATGGCAACATGATTTATAGCTACCACACAATGGAAAATCCATGC
              1060                1080                 1100                 1120
```

FIG.3A

```
                380                                              390                                   400
CysProGlnAsnAsnAspLeuGlySerLysSerGlyLysIleThrCysProLeuSerGluAspAsnGluHisVal
TGCCCCCAGAACAATGATCTGGGCAGCAAGAGTGGAAAGATTACTTGCCCCTTGTCAGAAGATAACGAGCATGTT
            1140                 1160                1180                  1200
                        410                                       420
GlnLysLysAlaLeuMetAspThrIleProValIleValLysIleLeuGluGluValGlnPheIleAlaMetArg
CAAAAAAAAGCTTTAATGGATACCATCCCAGTGATTGTGAAGATACTGGAGGAAGTTCAGTTCATAGCAATGCGC
            1220                 1240                1260
                  430                                      440
PheArgLysGlnAspGluGlyGluGluIleCysSerGluTrpLysPheAlaAlaAlaValIleAspArgLeuCys
TTCAGGAAGCAAGATGAGGGTGAAGAGATCTGCAGTGAGTGGAAGTTTGCAGCTGCTGTCATAGACAGATTATGC
      1280                 1300                 1320                  1340
                              460                                   470
LeuValAlaPheThrLeuPheAlaIleIleCysThrPheThrIleLeuMetSerAlaProAsnPheIleGluAla
CTGGTTGCGTTTACCCTTTTTGCCATCATTTGCACATTTACAATACTCATGTCTGCTCCCAACTTTATAGAAGCT
       1360                 1380                 1400                 1420
             480
ValSerLysAspPheThrEnd
GTTTCAAAGGATTTTACGTAAGGATTTCAAATATGAACACAATGAGCTGAAAGGTAACTTAAAAGTGAATATCAT
            1440                 1460                1480                  1500
CAGTACTATTGCTAGATAGTTTAAACTCAAAACAGAGAAGTGTACTTTTATGTGCTGACATACACAGAAGGGGAT
                  1520                 1540                1560
AAAATTAATTTCAGGAGATAATTATTTCTGATGTTAGTAATAGTAGTTACTGAATAGTATACATACTGACCTCTT
       1580                 1600                 1620                  1640
ACTTATTTCCTAGGTGACTGCCACACATAATTATGTTATCATCTGCTACAAAAATAGAAAAGAATCCAAATCCAC
         1660                1680                 1700                  1720
GGTGTATTTATTAGAAGTTAACACCAGTGTAAATGTGTTATTGTATCTTTGTGGACTTCTAAATGTTGTAATAAT
             1740                1760                 1780                  1800
TTAAATGATAGATTAATGACTAGAAGTAGCATTTTGTTGTTTTCAATATCTTTATGTTTTATCATATTTGTTTAA
              1820                 1840                1860
TGTGGCTGTGACATTTACTTCTCAGATTTGACAGGCATCTCTCCGCAGTTTTATGATGCTGCATATTGCATAAAG
         1880                 1900                1920                  1940
GAATTC
```

RECOMBINANT DNA ENCODING NEURONAL α-BUNGAROTOXIN-BINDING PROTEINS

This invention was made with Government support under Contract DAMD17-86-C-6148 awarded by the Department of the Army. The Government has certain rights in this invention.

FIELD OF THE INVENTION

The present invention relates generally to neuronal α-bungarotoxin-binding proteins (αBgtBPs). More particularly, the present invention is directed to a family of vertebrate, such as avian or mammalian, neuronal αBgtBPs. In one aspect, the present invention relates to the isolation and sequencing of cDNA clones encoding two neuronal α-bungarotoxin-binding protein (αBgtBP) subunits: αBgtBP α1 and α2. The invention further relates to the identification and characterization of the α1 and α2 subunits, to the recognition and subtypes of αBgtBPs which use different α subunits, and to the expression of these subunits or their subsegments, as proteins in microorganisms or cell lines, particularly using recombinant DNA technology. In another aspect, the present invention concerns the use of cDNA clones encoding neuronal αBgtBP α1 and α2 subunits as probes that can, for example, identify further neuronal αBgtBP subunits. In a still further aspect, the invention relates to the use of neuronal αBgtBP and, in particular, the α1 and α2 subunits as diagnostic tools in the screening of cholinergic agents and other drugs that may affect the ligand binding, ion channel or other activity of intact neuronal αBgtBP subtypes.

BACKGROUND OF THE INVENTION

Since the neuronal αBgt binding proteins of the present invention and nicotinic acetylcholine receptors and certain other receptor types appear to be members of the same gene superfamily, it seems appropriate to start the review of background art with a brief overview of our recent knowledge of the known types of such receptors.

The study of cell to cell contacts known as synapses, has long been a focal point of neuroscience research. This is particularly true of the neuromuscular synapse (often called neuromuscular junction), which occurs at the point of nerve to muscle contact, primarily because of its accessibility to biochemical and electrophysiological techniques and because of its elegant, well defined structure. Much of this research has concentrated on acetylcholine receptors because they are a critical link in transmission of signals from nerves to muscles. Action potentials propagated along a motor nerve axon from the spinal cord depolarize the nerve ending causing it to release a chemical neurotransmitter, acetylcholine. Acetylcholine binds to nicotinic acetylcholine receptor proteins located on post-synaptic muscle cells, triggering the brief opening of a cation channel through the receptor molecule and across the postsynaptic membrane. The resulting flux of cations across the membrane triggers an action potential that is propagated along the surface membrane of the muscle, thereby completing neuromuscular transmission and ultimately causing contraction of the muscle.

Several lines of evidence demonstrate that nicotinic acetylcholine receptors (AChRs) of muscle, brain and ganglia, belong to the same family and function as acetylcholine (ACh)-gated cation channels.

The most well-studied member of this family is the muscle-type AChR of the electric organs of *Torpedo californica* and related species, because electric organs contain much larger amounts of nicotinic acetylcholine receptors than muscle. Muscle-type nicotinic AChRs are composed of four kinds of subunits, including two α subunits which contain the ACh-binding sites, and must be both liganded to efficiently trigger opening of the cation channel, and one each of β, γ and δ subunits. The subunits are oriented like barrel staves in the order of αβαγδ around the central cation channel whose opening is regulated by binding of ACh to the α subunits. All of the AChR subunits have sequence homologies throughout their lengths which suggests that they evolved by gene duplication from a common ancestor and have similar basic structures. Evolution of muscle-type AChRs has been quite conservative; there is 80% sequence homology between α subunits of AChRs of the electric organs of *Torpedo californica* and human muscle, and about 55% homology of the other subunits between these species. However, AChRs of different origin are much more antigenically distinct than their sequence homologies would suggest. A concise review of the structure and properties of muscle-type nicotinic AChRs is, for example, provided by Lindstrom et al, *Mol. Neurobiol.* 1(4), 281 (1987). Study of these receptors has been greatly enhanced by the availability of suitable molecular probes, in particular α-Bungarotoxin (αBgt). αBgt binds with great affinity to the ACh-binding sites of muscle-type nicotinic AChRs thereby inhibiting their function, and can be used as a histological label, affinity column ligand, and probe for the ACh-binding site of the purified AChRs. αBgt satisfies three criteria that certify it as a ligand for muscle-type AChRs: (i) its binding to muscle is saturable and agonists and antagonists of ACh compete for this binding; (ii) it binds to cells and regions of cells that respond physiologically to ACh; (iii) it blocks the physiological response of muscle to ACh.

Nicotinic acetylcholine receptors on neurons (neuronal nicotinic AChRs), that are members of the same ligand-gated cation channel family as muscle-type nicotinic AChRs, have originally been much less well characterized than have their muscle-type relatives. This was partly because there were no neural systems as convenient as muscle and there was no neural system that provided as much AChR as electric organs. Also, studies were hampered by lack of suitable molecular probes. As mentioned before, the snake toxin αBgt has proven an invaluable tool for characterizing muscle-type AChRs. Although it was originally inferred that αBgt binds to neuronal AChRs, later works made it clear that the αBgt receptors and neuronal acetylcholine receptors are not equivalent [see e.g. Carbonetto et al., *Proc. Natl. Acad Sci USA* 75, 2 (1978) on the non-equivalence of α-Bungarotoxin receptors and acetylcholine receptors in chick sympathetic neurons]. Since αBgt does not bind to neuronal nicotinic AChRs, it is not a useful probe for structural studies. More recently, monoclonal antibodies (mAbs) have proven extremely useful in studying neuronal AChRs. Immunoaffinity-purified neuronal AChRs were found to consist of only two kinds of subunits. The larger subunit was identified as the ACh-binding subunit by nicotine-blockable 4-(N-maleimido)benzyltri[$^3$H]-methylammonium iodide (MBTA) labeling after reduction, suggesting that it contains cysteines homologous to cysteines 192,193 of the muscle-type Torpedo AChR α subunits. The lower molecular weight subunit is often called the β subunit, but, more informatively, is also referred to as the structural subunit. The subunit stoichiometry is uncertain, but there are indications that it may be $x_2y_2$ (x and y standing for the ACh-binding and structural subunits, respectively). These subunits exhibit sequence homologies which indicate that they belong to the same gene family as the subunits of muscle-type nicotinic AChRs. There appear to be several subtypes of these AChRs, including at least four kinds of ACh-binding subunits and two kinds of structural subunits. Some different subtypes may use the same structural subunit and differ in which ACh-binding subunit they use. Schoepfer et al., Molecular Biology of Neuroreceptors and Ion Channels, NATO-ASI Series, H vol. 32, pp. 37–53 (1989), A. Maelicke (Ed.), Springer-Verlag, Heidelberg, and the references cited therein provide a comparison of the structures of muscle and neuronal nicotinic AChRs. Further details of the character of neuronal nicotinic AChRs from different sources (chicken brain, rat, bovine, human, etc.) and of the distribution of the two types of subunits can be found, for example, in Whiting and Lindstrom, *J. Neurosci.* 8(9), 3395 (1988), and Wada et al., *J. Comp. Neurol.* 284, 314 (1989).

Some receptors for glycine and γ-aminobutyric acid, such as the strychnine-binding glycine receptor of the spinal cord and the brain γ-aminobutyric acid$_A$ (GABA$_A$), are ligand-gated anion channels which appear to be more distant members of the same receptor superfamily which includes nicotinic receptors and may include other ligand-gated ion channels such as some receptors for glutamate and serotonin. Barnard et al., *Trends Neurosci.* 10, 502 (1987) compare the primary structures of the brain GABA$_A$ receptor, one of the subunits of the spinal cord glycine receptor and those of muscle-type and neuronal nicotinic AChRs.

Other neurotransmitter receptors whose subunit cDNAs have been cloned, are characterized as receptors without intrinsic ion channels. These receptors act through a GTP-binding protein and various enzymes to produce second messengers. All these receptors have a single subunit with sequence homology to rhodopsin. Typical representatives of this group are muscarinic AChRs and adrenergic receptors. Muscarinic AChRs are distinguished by their differential sensitivity to the alkaloid compound muscarine, and regulate a broad range of physiological and biochemical activities throughout the central and autonomic nervous systems via the activation of guanine nucleotide binding (G) proteins. A good summary of the recent knowledge about the structural and biochemical diversity of muscarinic AChRs is provided by Peralta et al., TIPS-February supplement, 6 (1988). Subtype-specific agonist and antagonist binding characteristics of chimeric $\beta_1$ and $\beta_2$-adrenergic receptors are disclosed by Frielle et al., *Proc. Natl. Acad. Sci. USA* 85, 9494 (1988).

As mentioned before, the neuronal AChRs exhibit high affinity for nicotine and other cholinergic agonists, but do not bind βBgt. Binding studies using the technique of autoradiography to produce detailed maps of [$^3$H]nicotine, [$^3$H]ACh and [$^{125}$I]αBgt labeling in near-adjacent sections of rat brain have revealed that whereas [$^3$H]nicotine and [$^3$H]ACh bind with strikingly similar pattern, there is remarkably little overlap with [$^{125}$I]αBgt labeling [Clarke et al., *Journal Neurosci.* 5, 1307 (1985)]. Based upon their experiments, that were in excellent agreement with previous works on αBgt binding in rodent brain, Clarke et al. concluded that αBgt may label a new kind of nicotinic receptors, that is clearly different from nicotinic AChRs. These receptors are usually referred to in the literature as neuronal αBgt binding proteins (αBgtBPs). Their concentration throughout the vertebrate brain is considerably higher than that of neuronal AChRs. A number of laboratories have documented the existence of αBgtBPs in sympathetic ganglion membranes and membrane fragments derived from vertebrate brain. Since the ability of cholinergic ligands to effect receptor function remained unknown and αBgt was found to have no effect on agonist-induced activation of acetylcholine receptors in these tissues, the identity of the toxin-binding component was entirely uncertain. The binding of αBgt to a clonal rat sympathetic nerve cell line was described by Patrick, J. and Stallcup, W., *J. Biol Chem.* 252, 8629 (1977). The binding was found to be saturable and was inhibited by a variety a cholinergic agonists and antagonists. In assays determining the binding constants for various cholinergic ligands no correlation was found between their ability to affect cholinergic function and to inhibit binding of αBgt. It was found that the site at which cholinergic ligands affect AChR function is different from the site at which cholinergic ligands inhibit αBgt binding. The authors concluded that the αBgt binding component is probably a single molecular species of an integral membrane protein which is different from the functional neuronal nicotinic AChR.

Carbonetto et al., Supra delivered evidence that the αBgt receptors in chick sympathetic neurons are not neuronal AChRs. Similar results were reported by Smith et al., *J. Neurosci.* 3, 2395 (1983) and Jacob et al., *J. Neurosci.* 3, 260 (1983) on chick ciliary ganglion neurons. The major findings in these articles are that neuronal levels of ACh sensitivity do not correlate with αBgt binding sites, and in the case of chick ciliary ganglion cells the αBgtBPs, unlike neuronal nicotinic acetylcholine receptors, are not located at synapses. Although Smith et al. have ruled out some trivial reasons for the lack of correlation between ACh sensitivity and αBgt binding, they or Jacob et al., Supra provide no explanation of the function of the αBgt binding site.

Conti-Tronconi et al., *Proc. Natl. Acad. Sci. USA* 82 (1985) purified αBgt-binding proteins from chick optic lobe and brain under conditions that were designed to minimize proteolysis. Five different peptides with molecular weights ranging between about 48,000 and about 72,000 were separated by gel electrophoresis and submitted to amino-terminal amino acid sequencing. The amino-terminal amino acid sequence of the 48,000 molecular weight subunit was found to be highly homologous to the sequences of known α subunits of peripheral AChRs from Torpedo electroplax, Electrophorus electroplax and muscle, and calf muscle. Amino-terminal amino acid sequence analysis of the other isolated protein fragments did not yield any signal above the high background consistently present, indicating that these fragments probably had blocked amino termini. Although there are some indications that the protein fragments not sequenced may be part of the same receptor, the subunit structure of brain αBgtBPs has not been established. Conti-Tronconi et al., Supra add to the confusion concerning the terminology, identity, and function of vertebrate αBgt binding proteins by concluding that brain αBgtBPs are nicotinic AChRs.

Whiting, P. and Lindstrom, J., *Proc. Natl. Acad. Sci. USA* 84, 595 (1987) report the purification of an αBgtBP from rat brain and the identification of four kinds of subunits. The four polypeptides separated by affinity-purification of the αBgtBP were similar in their apparent molecular weights to the α, β, γ and δ subunits of muscle-type nicotinic AChRs. In the absence of antibody probes for the toxin binding protein, the authors could not unequivocally demonstrate that each of the four polypeptides were true constituents of the same macromolecule.

Like muscle and neuronal AChRs, αBgtBPs can be affinity labeled with MBTA after reduction with dithiothreitol (DTT). In chicken brain this labels a subunit of apparent molecular weight of 45,000. This suggests that, as in nicotinic AChRs, there is a readily reducible disulfide bond near the ACh binding site. The ACh-binding subunits of all nicotinic AChRs characterized to date exhibit a pair of cysteines homologous to the disulfide-bound pair at α192, 193 in muscle-type AChR α subunits which are known to be affinity labeled by MBTA.

Norman et al., *Proc. Natl. Acad. Sci. USA* 79, 1321 (1982) report the isolation of the αBgtBP from chick optic lobe as a pure glycoprotein and compare this protein with the αBgt-binding component isolated from the rest of the chick brain. The authors conclude that the αBgtBP from chick optic lobe and the αBgtBP from the rest of the brain appear similar or identical by a series of criteria and are both related to peripheral AChRs. For further information see, for example: Kao et al., *J. Biol. Chem.* 259, 11662 (1984); Kao et al., *J. Biol. Chem.* 261, 8085 (1986); Whiting, P. and Lindstrom, J., *FEBS Lett.* 213(1), 55 (1987); and Whiting et al., *FEBS Lett.* 219(2), 459 (1987).

The selected literature references cited hereinabove illustrate the controversial nature of our present knowledge about αBgtBPs. The following main observations have been made so far:

Vertebrate (avian and mammalian) brains contain both nicotinic AChRs which have high affinity for nicotine and acetylcholine but not for αBgt, and distinct αBgt-binding sites. There are more αBgtBPs than neuronal AChRs.

In some cases (chick ciliary ganglion cells, chick sympathetic ganglion cells, rat PC12 pheochromocytoma cells), αBgtBPs appear to be made by cells which also produce neuronal nicotinic AChRs, but these αBgtBPs do not appear to function as ACh-gated cation channels.

In the case of chick ciliary ganglion cells, the αBgtBPs are not located at synapses.

There are some claims of vertebrate neuronal AChRs whose function is blocked by αBgt, but so far they are not supported by conclusive evidence.

The αBgt-binding proteins from brains of chicks, and rats (similarly to muscle-type AChRs, and neuronal AChRs) can be affinity labeled with BAC and MBTA, after reduction with DTT. This suggests that amino acid residues homologous to Cys α192–193 of electric organ and muscle AChRs may have been conserved in the members of what appears to be an extended gene family consisting of muscle-type AChRs, neuronal AChR subtypes, and neuronal αBgtBPs.

The partial N-terminal amino acid sequence of one αBgtBP subunit of apparent molecular weight of 48,000 (Conti-Tronconi, et al., Supra) from chicken brain exhibits sequence homology with AChR subunits. This, along with pharmacological properties, is another indication that muscle-type and neuronal nicotinic AChRs and αBgtBPs are probably members of the same gene superfamily.

It is certain that neuronal αBgtBPs are functionally, structurally, immunologically, histologically, and pharmacologically distinct from functional vertebrate AChRs which do not bind αBgt.

However, the function of the αBgt-binding sites remains obscure. There is a large body of evidence indicating that the αBgtBPs which have been most carefully studied are not ACh-gated cation channels. Although there are indications that they may have several subunits, the subunit structure of αBgtBPs is unclear. The only information available in the art concerning the sequence of αBgtBP subunits, is a short N-terminal amino acid sequence of a polypeptide of the αBgtBP from chicken brain reported by Conti-Tronconi, et al., Supra.

SUMMARY OF THE INVENTION

Starting with an oligonucleotide probe based on the N-terminal amino acid sequence reported by Conti-Tronconi et al., Supra for an αBgtBP subunit from chick brain, cDNA clones have been identified which code for a protein of 502 amino acids, having a deduced molecular weight of 56,950 (with a mature peptide lacking a signal sequence of 54,550) that has been identified as a subunit of a brain αBgtBP. In one aspect, the present invention relates to the above cDNAs and to the encoded subunit, hereinafter termed the αBgtBP α1 subunit. Details of the clone names and methods involved are reported in the Examples, in particular in the Experimental Procedures section.

Using fragments of the cDNA αBgtBPα1 as probe, another closely related homologue cDNA clone was isolated from a chick brain cDNA library, encoding a 511 amino acid-containing protein with a molecular weight of 58,710 (putative mature peptide: 55,230). The encoded protein was identified as another αBgtBP subunit. In another aspect, the present invention relates to the above cDNA and to the encoded second subunit, hereinafter termed αBgtBPα2 subunit. Details of the clone names and methods are reported in the Examples, in particular in the Experimental Procedures section.

In another aspect, the present invention relates to the production of the α1 and α2 αBgtBP subunit proteins and fragments thereof by methods of recombinant DNA technology.

In a further aspect, the present invention concerns the use of cDNA clones encoding the neuronal αBgtBP α1 and α2 subunits as probes that can, for example, identify further neuronal αBgtBP subunits in chickens and other species such as humans.

In a still further aspect, the invention relates to the use of neuronal αBgtBP and, in particular, the α1 and α2 subunits as diagnostic tools in the screening of cholinergic and other drugs that may affect the ligand binding, ion channel or other activity of intact neuronal αBgtBP subtypes.

The present invention is directed to the above aspects and all associated methods and means for accomplishing such. For example, the invention includes the technology requisite to screening genomic cDNA libraries, nucleotide sequence determination, the preparation of antisera to αBgtBP, etc. The invention further includes the use of an expression system suitable for preparing substantial amounts of αBgtBP subunit peptides for use as immunogens for preparing antisera and monoclonal antibodies to native αBgtBP, to permit affinity purification of subtypes, and their histological location.

The present invention provides critical groundwork for practical applications and future studies of neuronal αBgt-BPs.

For the first time, the sequences of αBgtBP subunits have been determined, proving that this protein is a member of the AChR gene family and that subtypes exist.

The cDNA clones of the present invention, probably in combination with other related cDNA clones for further αBgtBP structural subunits, should allow the recombinant production of intact αBgtBP in suitable recombinant expression systems. This will permit evaluation of the function of this protein, e.g. whether it will function as a ligand-gated ion channel after appropriate post-translational modifications or in the presence of appropriate cofactors, and permit determination of the endogenous ligand (which may not be ACh) for this αBgtBP. Expression systems will also permit assay of the effects of cholinergic and other drugs on ligand binding and ion channel or other activity of intact αBgtBP subtypes.

Furthermore, the cDNA sequences of the present invention provide probes for identifying the remaining subunits of neuronal αBgtBPs from chicken brain but also from other species including human. These nucleic acid probes can also provide peptides useful for making antibody probes. Human cDNA probes may ultimately prove useful for identifying altered sequences in genetic diseases.

BRIEF DESCRIPTION OF THE DRAWINGS

FIG. 1A shows the deduced N-terminal amino acid sequences of the α1 and α2 αBgtBP subunits of the present invention, in alignment with the chemically determined N-terminal amino acid sequence published by Conti-Tronconi, et al., Supra. cDNA-deduced amino acids identical with the published protein sequence are marked by *.

FIGS. 1B and 1C illustrate the αBgtBP α1 and α2 subunits, in comparison with ACh-binding subunits of chicken AChRs.

FIGS. 2A and 2B show the nucleotide sequence and the deduced amino acid sequence of the α1 subunit. The mature protein starts at position +1. The underlined sequence was also confirmed by polymerase chain reaction (PCR) as described in the Examples.

FIGS. 3A and 3B illustrate the nucleotide sequence and the deduced amino acid sequence of the α2 subunit. The putative mature protein starts at position +1.

FIG. 4 summarizes the identification of the cDNA clones which led to the deduced sequences of the α1 and α2 subunits of αBgtBP.

FIG. 5 shows that antibodies to bacterially expressed fragments of proteins encoded by fragments of cDNAs for αBgtBP α1 and α2 subunits, in fact, bind to authentic αBgtBP in detergent extracts of chicken brains, and further shows that the αBgtBP α1 subunit is present in a subtype of αBgtBP, which accounts for about 75% of the total, whereas the αBgtBP α2 subunit is present in a subtype which accounts for less than 20% of the total αBgtBP in brain extracts tested.

DETAILED DESCRIPTION OF THE INVENTION

1. Definitions

The amino acids, which occur in the various amino acid sequences referred to in the specification have their usual, three- and one-letter abbreviations, routinely used in the art, i.e.:

| Amino Acid | Abbreviation | |
|---|---|---|
| L-Alanine | Ala | A |
| L-Arginine | Arg | R |
| L-Asparagine | Asn | N |
| L-Aspartic acid | Asp | D |
| L-Cysteine | Cys | C |
| L-Glutamine | Gln | Q |
| L-Glutamic Acid | Glu | E |
| L-Glycine | Gly | G |
| L-Histidine | His | H |
| L-Isoleucine | Ile | I |
| L-Leucine | Leu | L |
| L-Lysine | Lys | K |
| L-Methionine | Met | M |
| L-Phenylalanine | Phe | F |
| L-Proline | Pro | P |
| L-Serine | Ser | S |
| L-Threonine | Thr | T |
| L-Tryptophan | Trp | W |
| L-Tyrosine | Tyr | Y |
| L-Valine | Val | V |

As used herein, "AChR" stands for acetylcholine receptor, including muscle-type and neuronal nicotinic acetylcholine receptors, and "ACh" for acetylcholine.

As used herein, "αBgt" stands for α-Bungarotoxin, and αBgtBP for α-Bungarotoxin-binding proteins, in particular neuronal α-Bungarotoxin-binding proteins.

The term "mAbs" as used in the specification and claims, stands for monoclonal antibodies.

The term "expression vector" includes vectors capable of expressing DNA sequences contained therein, where such sequences are in operational association with other sequences capable of effecting their expression, i.e. promoter sequences. "Operatively harboring" means that the DNA sequences present in the expression vector work for their intended purpose. In general, expression vectors usually used in recombinant DNA technology are often in the form of "plasmids", i.e. circular, double stranded DNA loops which in their vector form, are not bound to the chromosome. In the present specification the terms "vector" and "plasmid" are used interchangeably. However, the invention is intended to include other forms of expression vectors as well, which function equivalently.

2. Deposits

Plasmid DNAs containing cDNA inserts encoding the α1 and α2 subunits of αBgtBP were deposited at the American Type Culture Collection (Rockville, Md.) under deposition numbers shown below. As explained in Examples and Experimental Procedures and shown in FIG. 4, clones pCh34-1 and pCh29-3 together encode αBgtBPα1, whereas the entire coding sequence of αBgtBPα2 is included within clone pCh31-1.

| Clone | Encodes | ATCC No. |
|---|---|---|
| Plasmid DNA, pCh29-3 | αBgtBPα1 N-terminal part | 40641 |
| Plasmid DNA, pCh34-1 | αBgtBPα1 C-terminal part | 40639 |
| Plasmid DNA, pCh31-1 | αBgtBPα2 | 40640 |

Said deposits were made, and accepted by ATCC, under the terms of the Budapest Treaty on the International Recognition of the Deposits of Microorganisms for Purposes of Patent Procedures and the regulations promulgated under said Treaty. Samples of said deposits will be available, in accordance with said Treaty and Regulations, to industrial property offices and other persons and entities legally entitled to receive them under the patent laws and regulations of the United States of America and any other nation or international organization in which the present application, or an application claiming priority of the present application, is filed. All restrictions on the public availability of samples of said deposits will be irrevocably removed, at the latest upon issuance of a United States patent on this application.

The foregoing description and the experimental details set forth in the following Example disclose a methodology that was initially employed by the present researchers in identifying and isolating particular neuronal αBgtBP subunits. Anyone with ordinary skill in the art will recognize that once this information, including the cDNA and protein sequences, and characterization and use of these receptor subunits, is available, it is not necessary to repeat the technical details disclosed herein to reproduce the present invention. Instead, in their endeavors to reproduce this work, they may choose convenient and reliable alternative methods that are known in the art. For example, they may synthesize the underlying DNA sequences for deployment within similar or other suitable, operative expression vehicles. The sequences herein may be used to create probes (e.g. as illustrated in the Example), preferably from regions at both the N- and the C-termini, to screen genomic libraries for further cDNA fragments. Furthermore, the sequence information herein may be used in cross-hybridization procedures to isolate, characterize and deploy DNA encoding αBgtBPs or their subunits from various species, including human.

Thus, in addition to supplying details of the procedures actually employed, the present disclosure serves to enable reproduction of the disclosed specific receptor subunits and other, related subunits and/or receptors, using means within the skill of the art having benefit of the present disclosure. All of such means are included within the enablement and scope of the present invention.

3. Example

A. Cloning of αBgtBP cDNAs

Figure 1A:
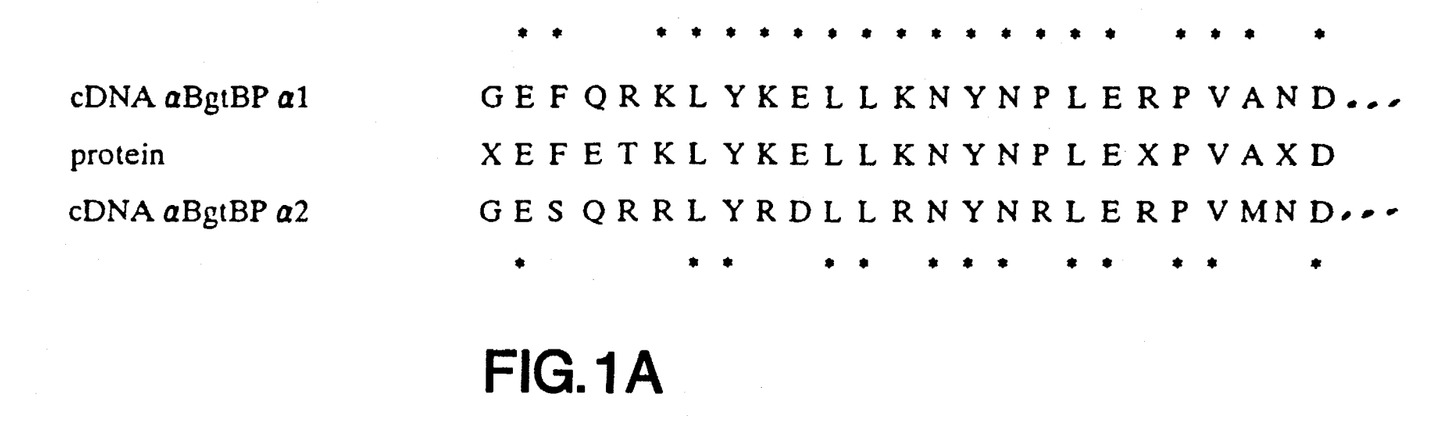
Figure 2B:
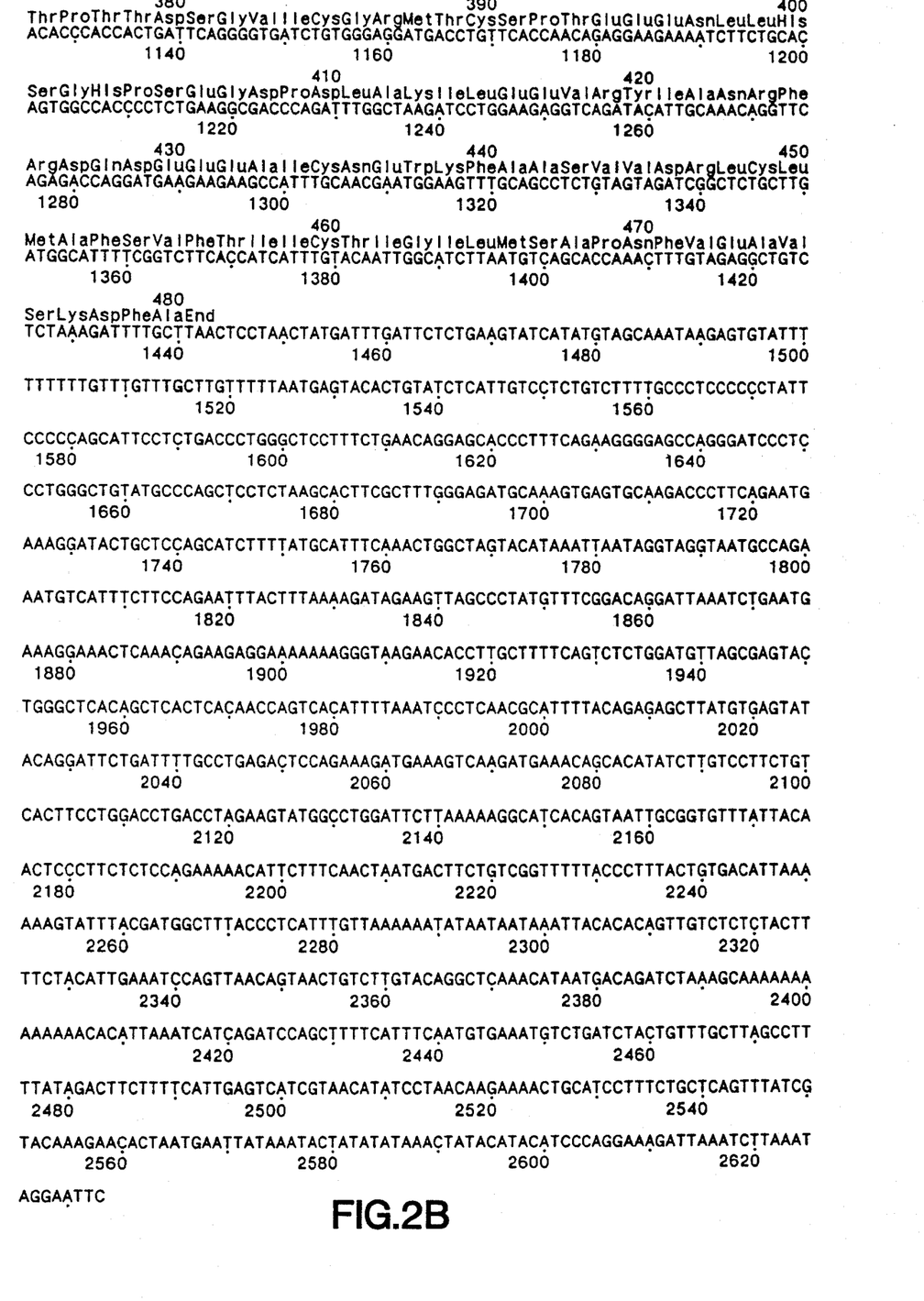

Using a 47-mer oligonucleotide of sequence 5'GGGTTG-TAGTTCTT$_C{}^G$AG$_G{}^C$AGCTGCTTGTA$_G{}^-$$^C$AGCTTGGTCTGGAACTG 3' designed on the previously chemically determined N-terminal protein sequence of a subunit of a toxin-affinity-purified αBgtBP (Conti-Tronconi et al., Supra), clone pCh29-1 has been isolated from a chick brain E17 cDNA library [Schoepfer et al., Neuron 1, 241 (1988)]. The deduced amino acid sequence in one reading frame was found to be identical to the chemically determined protein sequence in 20 of 22 residues, as shown in FIG. 1A. (In the Conti-Tronconi sequence the residues marked by "X" were not identified.) The same reading frame codes further 5' for a peptide with the characteristics of a leader peptide and has an open reading frame further 3' (FIGS. 2A and 2B). This open reading frame codes for amino acids (aa)-22 through 179 in FIGS. 2A and 2B. Thus, a partial cDNA clone coding for a subunit of a brain αBgtBP has been identified. For further characterization clone Ch29-3 was used. pCh29-3 is a subclone of pCh29-1, and contains all the sequences coding for the N-terminal fragment of the αBgtBPα1 subunit found in pCh29-1. pCh29-3 lacks further 5', untranslated sequences found in pCh29-1 which were only partially characterized. Since this clone is fully characterized, and was used in further experiments, pCh29-3 was deposited with ATCC. Another cDNA clone (pCh34-1) which encodes the remainder of the αBgtBPα1 sequences was identified later, as described in Experimental Procedures and depicted in FIG. 4. The protein fragment encoded by pCh29-3 together with the fragment encoded by pCh34-1 (then termed pCh29/34) are fragments of a protein of 502 aa with a deduced molecular weight of $M_r$=56,950 (mature peptide $M_r$=54,550).

Figure 1B:
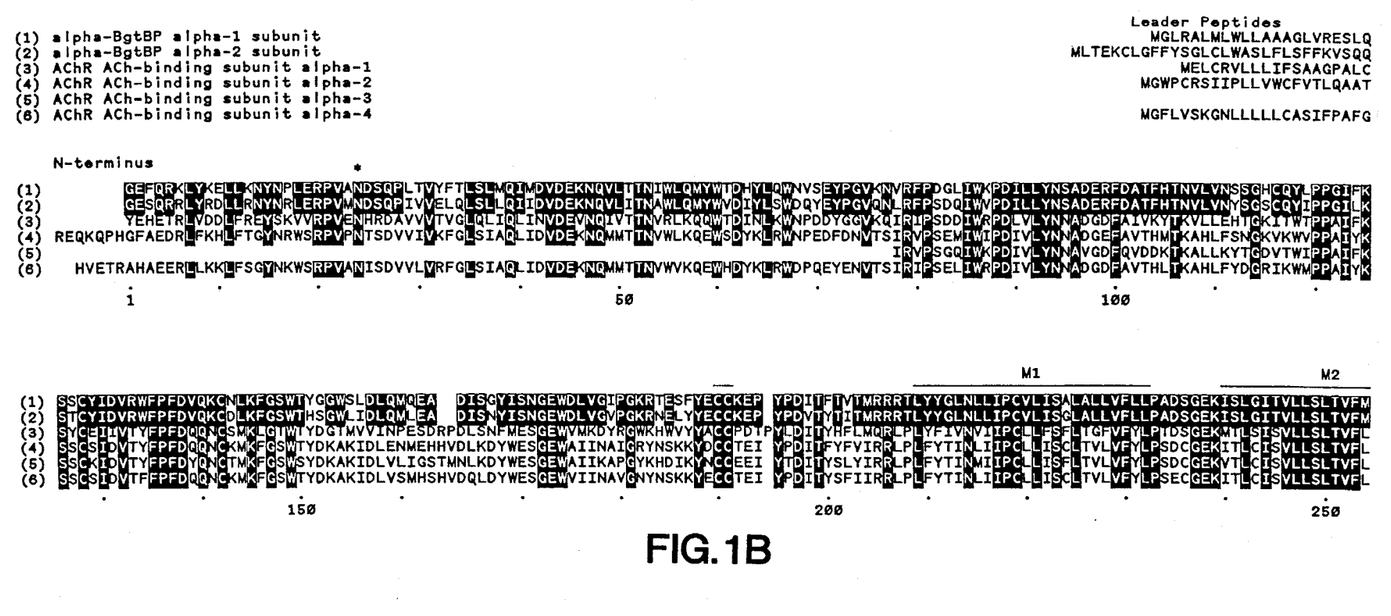
Figure 1C:
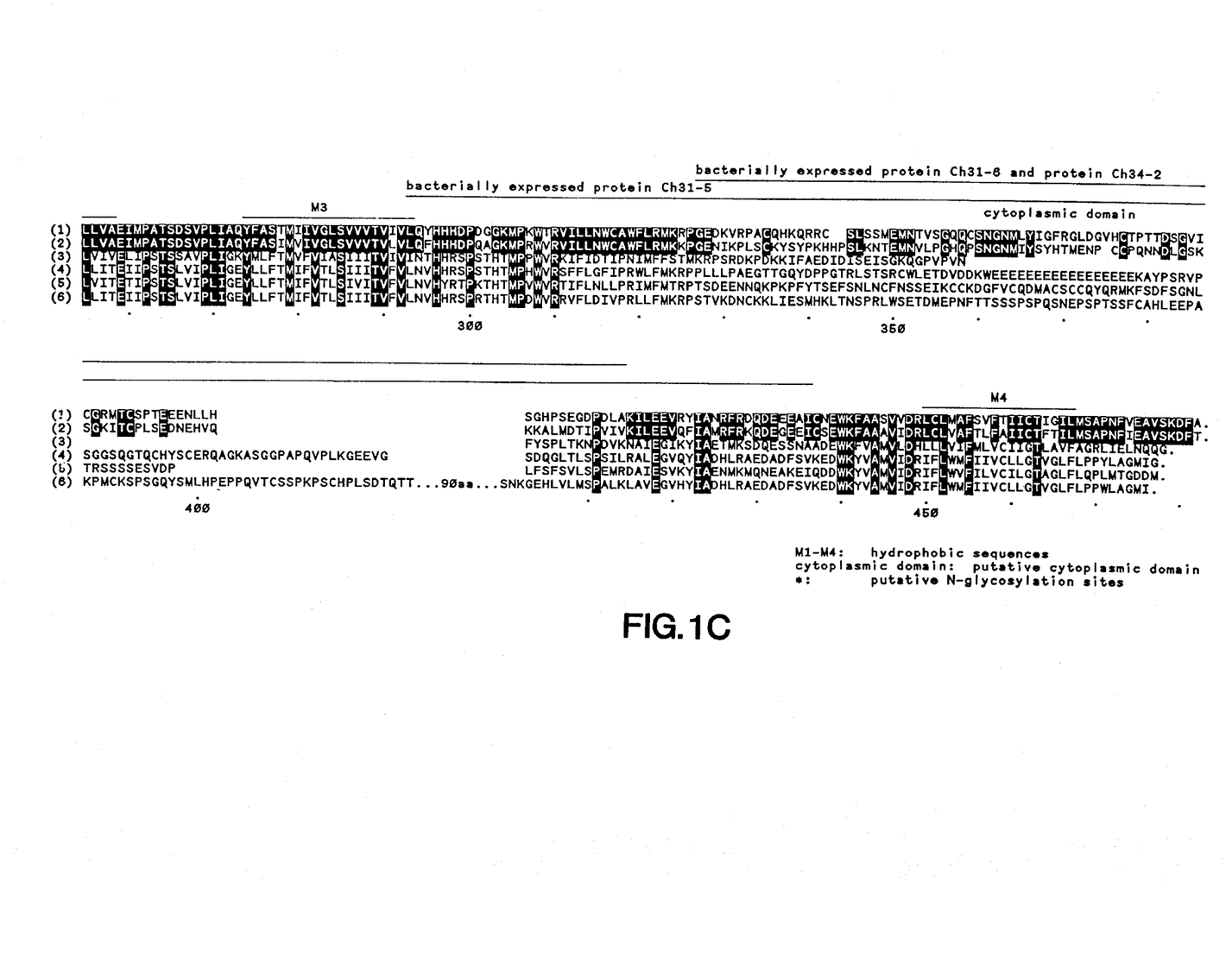

The protein has the general features of a subunit of a ligand-gated ion channel (FIGS. 1B and 1C): four hydrophobic segments termed M1-4, with M1-3 found very close together; a pair of cysteines spaced by 13 aa (128 and 142 in FIG. 1B); and some amino acids conserved throughout ligand-gated cation and anion channels. FIGS. 1B and 1C show only the alignment with brain AChR ACh-binding subunits. Because the pCh2934-encoded sequence shows the pair of adjacent cysteines characteristic of ACh-binding subunits, which have conventionally been termed "α," this subunit was termed the αBgtBP α1 subunit.

Another cDNA clone (pCh31-1) was isolated by low-stringency screening with fragments of Ch29-1. This encodes a complete sequence for the αBgtBP α2 subunit, and fragments corresponding to the C-terminal part were used to identify the cDNA pCh34-1, which encodes the C-terminal part of αBgtBP α1 subunit, as summarized in FIG. 4, and detailed in Experimental Procedures. Clone pCh31-1 for the αBgtBP α2 subunit encodes a 511 aa protein with a molecular weight of $M_r$=58,710 (putative mature peptide $M_r$=55,230). The sequence has the same general features as the α1 subunit. Without signal peptides, the α1 and α2 subunits are 62% identical overall (FIGS. 1B and 1C); most of the divergent amino acids are found in the putative cytoplasmic loop between aa 329 and 414, which shows basically no conservation except for stretches of five and three aa. Interestingly, α1 and α2 also differ significantly in their first 23 amino acids. In the N-terminal amino acid sequence of α2, there are only 13 amino acids out of 22 that are identical to the Conti-Tronconi sequence (FIG. 1A).

Figure 3B:
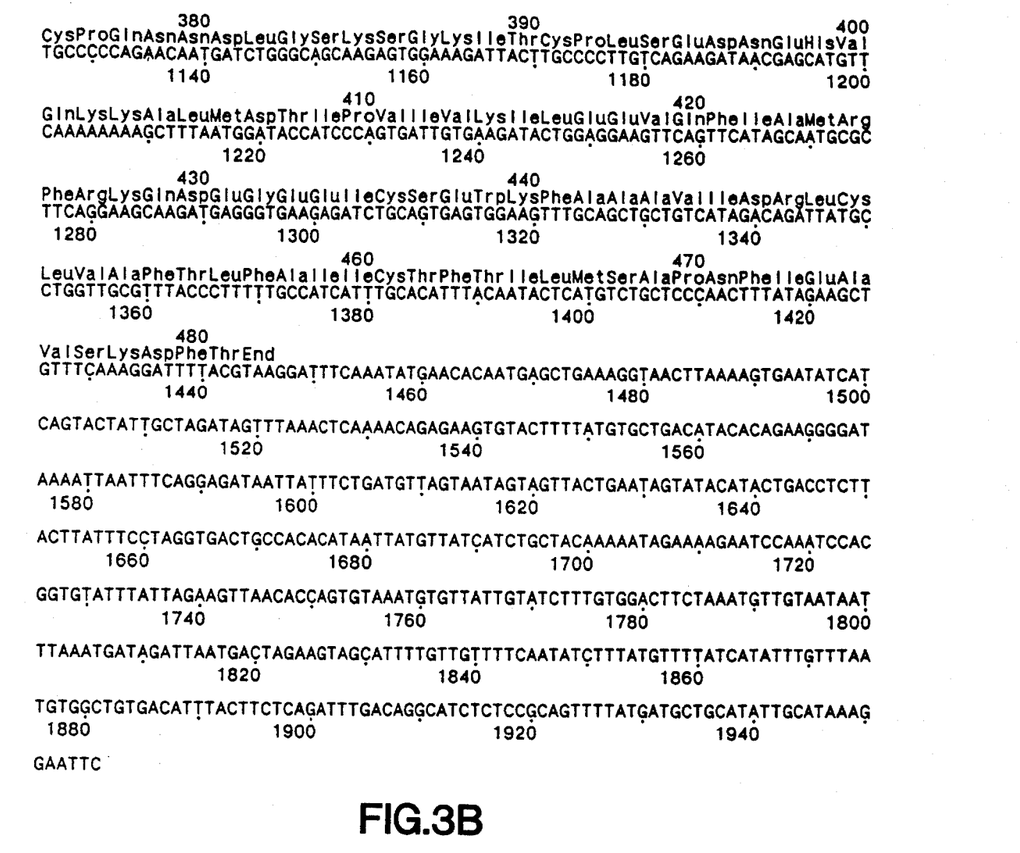

The nucleotide sequence of clone pCh31-1 together with the deduced amino acid sequence of the α2 subunit is illustrated in FIGS. 3A and 3B. The putative mature protein starts at position +1.

B. Subunit-Specific Antisera Tests

To critically test whether these cDNAs coded for subunits of authentic αBgtBP, cDNA sequences corresponding to amino acids 327 to 412 of αBgtBPα1, and 293 to 435 of αBgtBPα2 were expressed in bacteria, antisera were raised to unique peptide sequences encoded by these cDNAs, and the antisera obtained were tested for their ability to recognize native αBgtBP in detergent extracts of chicken brains.

Rats immunized with protein Ch31-5, a recombinant protein corresponding to the putative large cytoplasmic loop between M3 and M4 of the αBgtBP α2 subunit, developed high titer antisera against genuine chicken brain αBgtBP after a few weeks. Subsequently, mAbs were isolated which could bind to native αBgtBP. After sequencing the αBgtBP α1 subunit, we realized that protein Ch31-5 (α2 subunit) might have some epitopes in common with the αBgtBP α1 subunit. Therefore, mAbs raised against protein Ch31-5 were also tested on Western blots against protein Ch31-6, a shorter fragment of the putative cytoplasmic loop unique to the αBgtBP α2 subunit. mAb 308 and other mAbs not shown here bind to protein Ch31-6, thus they are specific for the αBgtBP α2 subunit, and possibly as yet unidentified subunits.

Polyclonal antisera against the unique cytoplasmic loop of the αBgtBP α1 subunit (pCh34-2) also recognized genuine brain αBgtBP.

Figure 5:
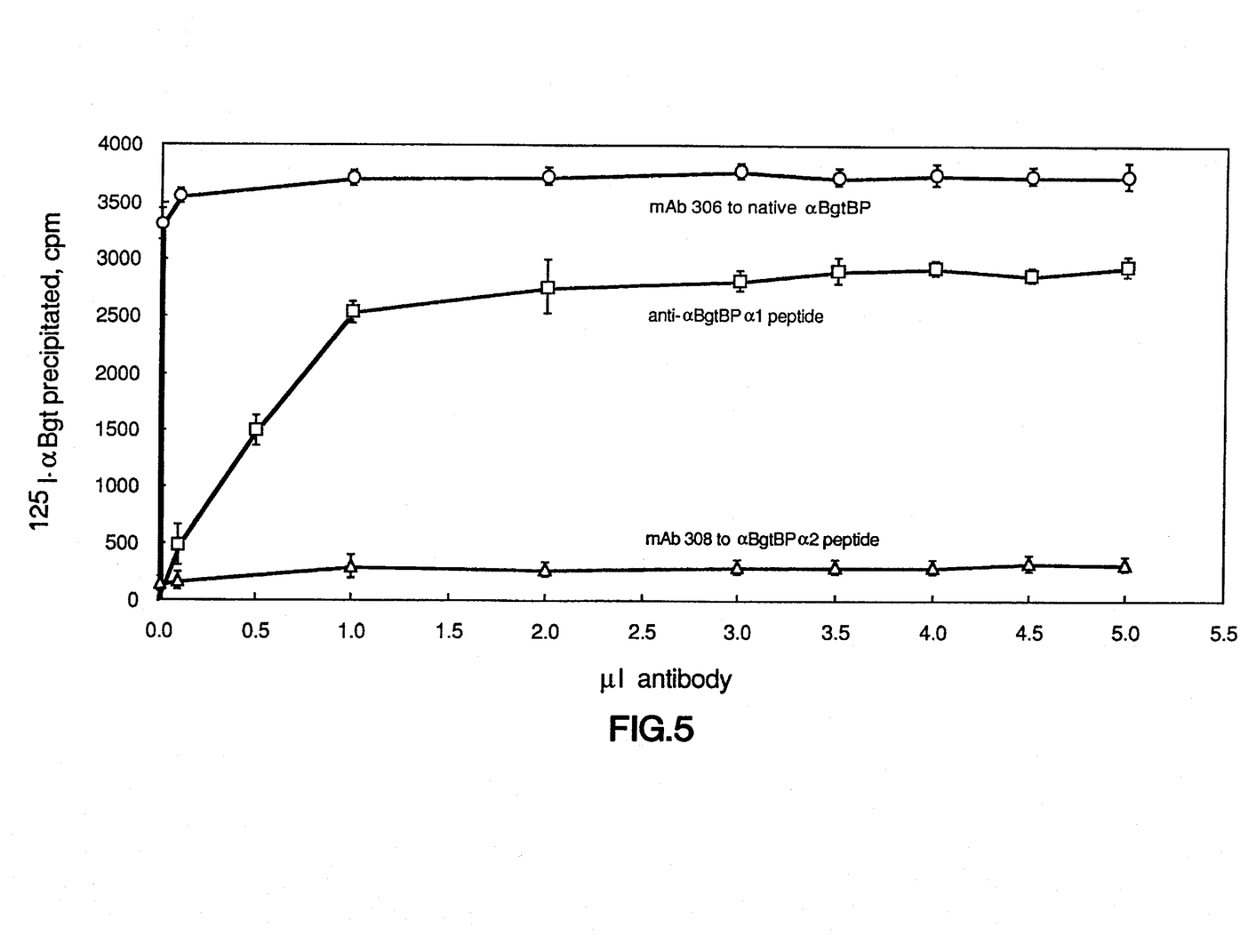

FIG. 5 shows immunoprecipitation of αBgtBP from brain extracts by antibodies to native αBgtBP and to fragments of α1 and α2 subunits of αBgtBP expressed in bacteria. mAb306 was raised to native affinity purified αBgtBP and binds to 100% of αBgtBP detectable in extracts of chicken brains. The subunit to which it binds is not known because its epitope is dependent on the native conformation of αBgtBP. Antisera to the bacterially expressed fragment of αBgtBP α1 subunit binds to a major subtype of αBgtBP which accounts for about 75% of the total. mAb 308 to the bacterially expressed fragment of αBgtBP α2 subunit binds to a minor subtype of αBgtBP which accounts for less than 20% of the total.

C. Experimental Procedures a. Cloning of αBgtBP Clones

Cloning was performed using standard procedures of recombinant DNA technology [see e.g. Maniatis et al., Molecular Cloning, A Laboratory Manual, Cold Spring Harbor: Cold Spring Harbor Laboratory (1982); and Berger, S. L. and Kimmel, A. R. (Eds.): Guide to molecular cloning techniques, *Meth. Enzymol.* 152 (1987)].

A cDNA library (Schoepfer et al., Neuron 1, 241 (1988) from embryonic day 18 (E18) chicken brains was screened with the 47-mer oligonucleotide designed on the chemically determined N-terminal protein sequence of one subunit of toxin-purified chicken brain αBgtBP (Conti-Tronconi et al., Supra), basically following codon usage frequencies.

Figure 4:
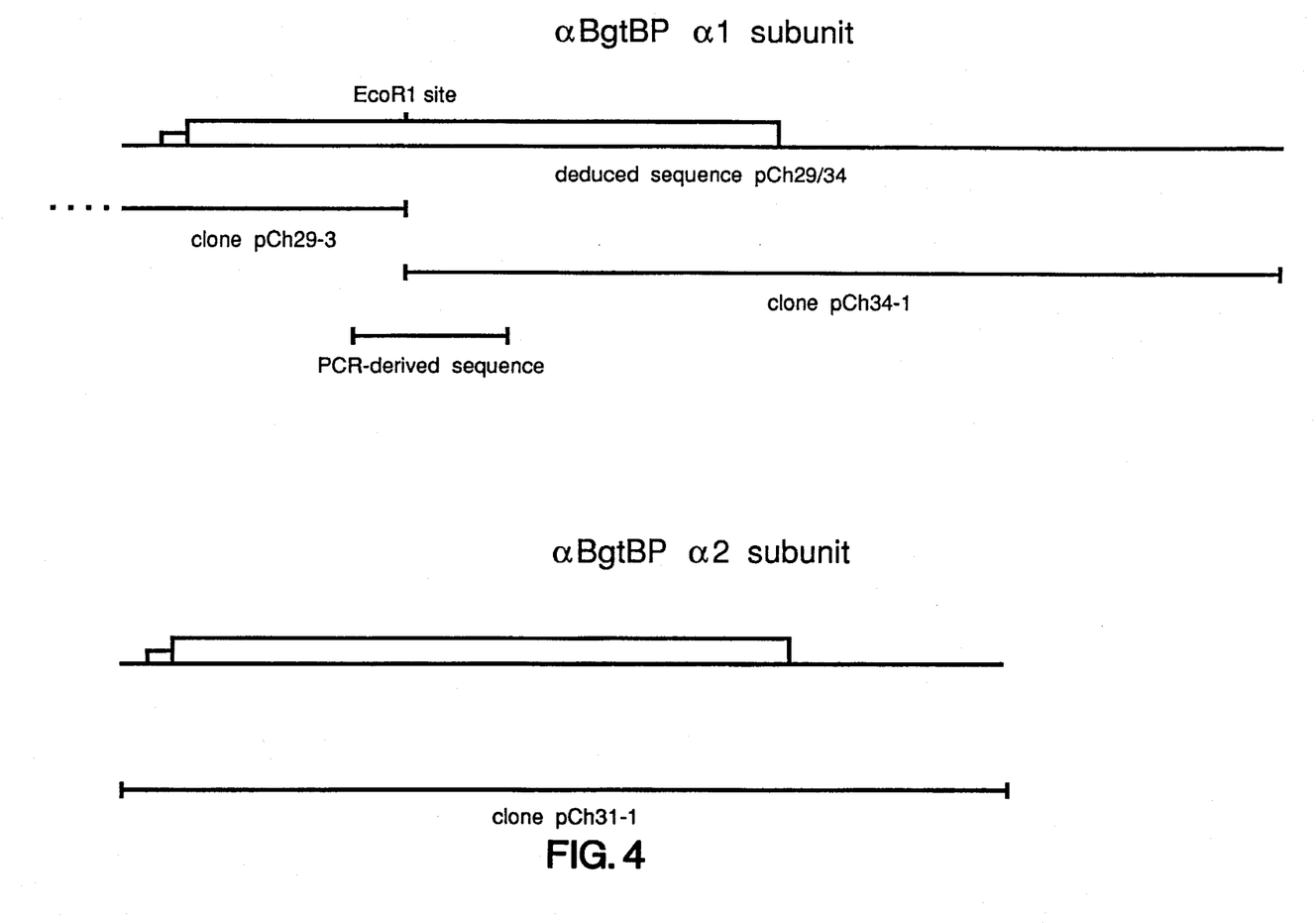

The procedures by which cDNAs for the α1 and α2 subunits of αBgtBP were identified is are shown in FIG. 4. Using the oligonucleotide based on the N-terminal amino acid sequence of an αBgtBP subunit, a clone termed pCh29-1 was identified. Due to the properties of the cDNA library used, this clone ends at an EcoRI site in the middle of the sequence encoding α1 subunit. This clone also contains extensive 5' untranslated sequences. Thus, a subclone, pCh29-3, was made which eliminates these untranslated sequences, but retains the sequences encoding the N-terminal part of the α1 subunit. Using this sequence as a probe, a cDNA, pCh31-1, was identified which encoded the entire sequence of α2. This provided a probe for identifying a clone for the C-terminal part of α1, pCh34-1. In order to show that the coding sequences of pCh29-3 and pCh34-1 were actually part of a single mRNA which was cleaved at an EcoRI site during cloning, a fresh avian mRNA preparation was used to produce cDNA, and then the polymerase chain reaction (PCR) primed with terminal oligonucleotides from pCh29-3 and pCh34-1 was used to amplify a sequence which proved to overlap the two clones and demonstrate that they derive from a single mRNA.

Stringency conditions were 30% formamide, 5×SSPE (1×SSPE is 0.18M NaCl, 0.01M NaPO$_4$, pH 7.4, and 1 mM EDTA) at 42° C. for hybridization, followed by final washings at 55° C., 1×SSPE (clone pCh29-1 was identified in this way). Using pCh29-1 or a fragment thereof (i.e. pCh29-3) as a probe, pCh31-1 was isolated, and subsequently, using pCh31-1 fragments as probes, pCh34-1 was isolated. The nucleotide sequences were completely determined in both strands. By deduced amino acid sequence homology to pCh31-1 and by common EcoRI sites (nucleotides 533–539, FIG. 2A) it is likely that pCh29-3 codes for the N-terminal and pCh34-1 for the C-terminal part of the α1 subunit. As apparently all cDNA EcoRI sites in this library were cleaved, the contiguousness of pCh29-3 and pCh34-1 was demonstrated by the polymerase chain reaction (PCR) technique [White et al., *Trends Genetics* 5, 185 (1989)]. Ca 300 ng E17 chicken brain first and second strand cDNA was subjected to 35 cycles (1 minute, 92.5° C.; 2 minutes, 55° C.; 1 minute 30 second, 72° C. on an Ericomp Temperature cycler) using Taq polymerase (Perkin Elmer) with the supplier's recommended buffer. The 5' primer (24-mer) sequence was derived from pCh29-3, the 3' primer (24-mer) sequence from pCh34-1. Plasmids containing the specific reaction product were sequenced (underlined in FIGS. 2A and 2B), proving to be identical between the primers used to pCh29-3 and pCh34-1 spliced together at the EcoRI site.

b. Antisera to αBgtBP

Fragments of pCh31-1 and pCh34-1 were subcloned into a T7 promoter-based bacterial expression system described by Rosenberg et al., Gene 56, 125 (1987). At least the cloning sites were sequenced for all constructs. The deduced protein sequences of the recombinant proteins are:

protein Ch34-2 (encoding a small, unique sequence of αBgtBPα1, see FIG. 1C):
MASMTGGQQMGRDPSSRSAGEDKVRPAC-QHKQRRCSLSSMEMNTVSGQQCSNGNMLY IGFR-GLDGVHCTPTTDSGVICGRMTCSP-TEEENLLHSGHPSEGDpDLANSKLDPAAN KARKEAELAAATAEQ protein Ch31-5 (encoding the large putative cytoplasmic domain of αBgtBPα2, see FIG. 1C):
MASMTGGQQMGRIKLRIPWYQLQFHHHD-PQAGKMPRWVRVILLNWCAWFLRMKKPGE NIKPLSCKYSYPKHHPSLKNTEMNV-LPGHQPSNGNMIYSYHTMENPCCPQNNDLGSK SGKITCPLSEDNEHVQKKALM-DTIPVIVKILEEVQFIAMRFRKQDEGEEIRLLTKPE RKLSWLLPPLSNN protein Ch31-6 (encoding a smaller, unique sequence of αBgtBPα2, see FIG. 1C):
MASMTGGQQMGRDPSSRSAGENI-KPLSCKYSYPKHHPSLKNTEMNVLPGHQPSNGNM IYSYHTMENPCCPQNNDLGSKSGKITC-PLSEDNEHVQKKALMDTIPVIVNSKLDPAA NKARKEAELAAATAEQ The underlined sequences are genuine to the deduced parent plasmid sequences, and the additional amino acids are vector-encoded.

Protein Ch34-2 was not found to form inclusion bodies. Therefore, SDS-PAGE-purified preparations were used for immunization of Lewis rats.

Protein Ch31-5 was obtained as inclusion bodies isolated by differential centrifugation. Impurities were successively extracted with 1M NaCl, 0.5% Triton X-100, and 3M KSCN, and then the inclusion bodies were solubilized in 8M urea. After removing the urea by dialysis, the partially soluble protein was more than 50% pure, as judged by Coomassie-stained SDS-PAGE. Lewis rats were immunized repeatedly with approximately 100 μg of protein in CFA.

Protein Ch31-6 was not purified for use as an immunogen, but only used as an antigen in Western blots, as described below.

c. Spleen Cell Fusion

The rat with the highest titer to protein Ch31-5 was immunized intraperitoneally, five days before the fusion, with 100 ng of protein Ch31-5 in PBS. On the day of the fusion the rat was killed and its spleen cells fused with Sp2/0 mouse myeloma cells using polyethylene glycol [Hochschwender et al., Production of rat×mouse hybridomas for the study of the nicotinic acetylcholine receptor, T. A. Springer, ed., New York: Plenum Publishing Corporation, pp. 223–238 (1985)]. Nine days after the fusion, the culture supernatants were screened in a radioimmunoassay for antibodies which bound $^{125}$I-αBgt-labeled αBgtBP in extracts of embryonic chick brain (see procotol below). Positive cultures were cloned twice by limiting dilution and then expanded to large cultures. These five hybridomas were designated as mAbs 308–312. Culture media was collected, concentrated by ultrafiltration and ammonium sulfate precipitation, and dialyzed against PBS containing 10 mM NaN$_3$.

d. Radioimmunoassay

Triton X-100 extracts of E18 chick brains were prepared according to the protocol described by Whiting and Lindstrom, Biochem 25, 2082 (1986). Antisera or mAb stock were diluted in PBS and incubated with 40 μl chick brain extracts containing 4 μl normal rat serum and 2 nM $^{125}$I-αBgt (specific activity 2–5×10$^{17}$ cpm/mol) in a total volume of 100 μl. After overnight incubation at 5° C., 100 μl goat anti-rat immunoglobulin was added and incubated for another hour. PBS-Triton X-100 was added (1 ml) and the immune complexes pelleted and washed twice with PBS-Triton. $^{125}$I-αBgt in the pellet was determined by ⌣ counting. Nonspecific and background counts were determined using preimmune serum and were subtracted from all data. Maximum binding of $^{125}$I-αBgt to αBgtBP in the extracts was determined by incubating 40 μl extract with 2 nM $^{125}$I-αBgt in a total volume of 100 μl. After overnight incubation at 5° C., 4 ml 10 mM Tris, 0.05% Triton X-100, pH 7.5, was added and the mixture rapidly filtered through Whatman GF/B filters pretreated with 0.3% polyethylenimine [Bruns et al., *Analyt. Biochem.* 132, 74–81 (1983)]. The filters were washed three times with 4 ml of the same buffer and counted. Nonspecific binding was determined in the presence of 1 mM carbamylcholine.

We claim:

1. An isolated DNA molecule, comprising a sequence of nucleotides encoding an α subunit of a neuronal α-bungarotoxin-binding protein (αBgtBP) subtype or a fragment of said subunit, wherein said DNA fragment is sufficiently homologous to the DNA of FIGS. 2A or 2B or FIGS. 3A and 3B to hybridize thereto under conditions of low stringency.

2. The DNA molecule of claim 1, wherein said subunit is the α1 subunit of the αBgtBPα1 subtype.

3. The DNA molecule of claim 1, wherein said subunit is the α2 subunit αBgtBPα2 subtype.

4. The DNA molecule of claim 2, encoding a protein of about 502 amino acids, having a molecular weight between about 54,550 and about 56,950, and an amino acid sequence essentially as set forth in FIGS. 2A and 2B.

5. The DNA molecule of claim 3, encoding a protein of about 511 amino acids, having a molecular weight between about 55,230 and about 58,710, and an amino acid sequence essentially as set forth in FIGS. 3A and 3B.

6. The DNA molecule of any of claims 1 to 5 which is a cDNA molecule.

7. The DNA molecule of any of claims 1 to 5 which is a recombinant DNA molecule.

8. A plasmid selected from the group consisting of pCh29-3, pCh34-1, and pCh31-1.

9. An expression vector operatively harboring DNA encoding an α subunit of a neuronal αBgtBP subtype or a fragment of said subunit, wherein said DNA is sufficiently homologous to the DNA of FIGS. 2A or 2B, FIGS. 3A and 3B to hybridize thereto under conditions of low stringency.

10. The expression vector of claim 9, wherein said subunit is the α1 subunit.

11. The expression vector of claim 9, wherein said subunit is the α2 subunit.

12. The expression vector of claim 10, wherein said DNA encodes a protein of about 502 amino acids, having a molecular weight between about 54,550 and about 56,950, and an amino acid sequence essentially as shown in FIGS. 2A and 2B.

13. The expression vector of claim 11, wherein said DNA encodes a protein of about 511 amino acids, having a molecular weight between about 55,230 and about 58,710, and an amino acid sequence essentially as shown in FIGS. 3A and 3B.

14. The expression vector of claim 10, comprising the cDNA clone pCh29-3, or pCh34-1.

15. The expression vector of claim 11, comprising the cDNA clone pCh31-1.

16. A recombinant host cell transfected with an expression vector of any one of claims 9 to 15.

17. The cell of claim 16 which is a prokaryote cell.

18. The cell of claim 17, wherein said prokaryote is a bacterium.

19. An isolated DNA molecule that encodes a protein that has the amino acid sequence set forth in FIGS. 2A and 2B or FIGS. 3A and 3B.

20. An expression vector, comprising the DNA of claim 11.

21. A recombinant host cell comprising the vector of claim 20.

22. An isolated DNA molecule that comprises a DNA fragment which encodes an α subunit of a chicken neuronal α-bungarotoxin-binding protein (αBgtBP) subtype, wherein said DNA fragment is selected from the group consisting of DNA fragments that are sufficiently homologous to the DNA of FIGS. 2A and 2B or FIGS. 3A and 3B to hybridize thereto under conditions of low stringency, DNA fragments that encode a protein that has the amino acid sequence set forth in FIGS. 2A and 2B or FIGS. 3A and 3B and DNA fragments that hybridize under conditions of low stringency to DNA fragments that encode a protein that has the amino acid sequence set forth in FIGS. 2A and 2B or FIGS. 3A and 3B.

* * * * *

UNITED STATES PATENT AND TRADEMARK OFFICE
CERTIFICATE OF CORRECTION

PATENT NO. : 5,599,709
DATED : February 4, 1997
INVENTOR(S) : Lindstrom, et al.

It is certified that error appears in the above-indentified patent and that said Letters Patent is hereby corrected as shown below:

Column 1, line 7, before the period (.), insert --and under NIH Grant No. R01 NS 11323--.

<u>IN THE CLAIMS</u>: Column 14, line 29, Claim 20, change "11." to --19.--.

Signed and Sealed this

Twenty-fourth Day of June, 1997

Attest:

BRUCE LEHMAN

Attesting Officer

Commissioner of Patents and Trademarks